United States Patent
Choudhury et al.

(10) Patent No.: US 11,291,750 B2
(45) Date of Patent: Apr. 5, 2022

(54) HYDROGEL CONDOM

(71) Applicant: THE TEXAS A & M UNIVERSITY SYSTEM, College Station, TX (US)

(72) Inventors: Mahua Choudhury, College Station, TX (US); Xiaofeng Kang, College Station, TX (US); Allison R. Ficht, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 0 days.

(21) Appl. No.: 16/079,466

(22) PCT Filed: Feb. 23, 2017

(86) PCT No.: PCT/US2017/019158
§ 371 (c)(1),
(2) Date: Aug. 23, 2018

(87) PCT Pub. No.: WO2017/147314
PCT Pub. Date: Aug. 31, 2017

(65) Prior Publication Data
US 2019/0060530 A1 Feb. 28, 2019

Related U.S. Application Data

(60) Provisional application No. 62/298,809, filed on Feb. 23, 2016.

(51) Int. Cl.
*A61L 31/14* (2006.01)
*A61F 6/04* (2006.01)
*A61K 31/352* (2006.01)
*A61K 9/00* (2006.01)
*A61K 9/127* (2006.01)
*A61L 31/04* (2006.01)

(52) U.S. Cl.
CPC .............. *A61L 31/145* (2013.01); *A61F 6/04* (2013.01); *A61K 9/0014* (2013.01); *A61K 9/127* (2013.01); *A61K 31/352* (2013.01); *A61L 31/042* (2013.01); *A61L 31/048* (2013.01)

(58) Field of Classification Search
None
See application file for complete search history.

(56) References Cited

U.S. PATENT DOCUMENTS 5,362,768 A 11/1994 Askari et al.
2005/0127552 A1* 6/2005 Modha .............. A61F 6/04
264/129

FOREIGN PATENT DOCUMENTS

JP 3847845 11/2006

OTHER PUBLICATIONS

Sun, Jeong-Yun, et al. "Highly stretchable and tough hydrogels." Nature 489.7414 (2012): 133.*
Jullian, Carolina, et al. "Complexation of quercetin with three kinds of cyclodextrins: an antioxidant study." Spectrochimica Acta Part A: Molecular and Biomolecular Spectroscopy 67.1 (2007): 230-234.*
Zhang, Wei, et al. "Antioxidant treatment with quercetin ameliorates erectile dysfunction in streptozotocin-induced diabetic rats." Journal of bioscience and bioengineering 112.3 (2011): 215-218.*
Chen, YongMei, et al. "Double network hydrogel with high mechanical strength: Performance, progress and future perspective." Science China Technological Sciences 55.8 (2012): 2241-2254.*
Najafi-Soulari, et al. Encapsulation optimization of lemon balm antioxidants in calcium alginate hydrogels, Journal of Biomaterials Science, Polymer Edition (2016) 27:16, 1631-1644.
Mewman, Tim. The hunt for the perfect condom continues, Medical News Today, Dec. 1, 2015, 1-5.
PCT International Search Report and Written Opinion dated May 25, 2017, Appl. No. PCT/US2017/019158, "Hydrogel Condom," filed Feb. 23, 2017, 7 pages.
Bellastella, G. et al. "Dimensions of human ejaculated spermatozoa in Papanicolaou-stained seminal and swim-up smears obtained from the Integrated Semen Analysis System (ISAS)" *Asian Journal of Andrology*, 2010, pp. 871-879, vol. 12.

* cited by examiner

*Primary Examiner* — John Pak
*Assistant Examiner* — Daniel L Branson
(74) *Attorney, Agent, or Firm* — Saliwanchik, Lloyd & Eisenschenk (57) ABSTRACT

A hydrogel condom containing an antioxidant can provide increased sexual pleasure, thus improving usage and resulting in prevention of disease and prevention of unwanted pregnancies.

11 Claims, 11 Drawing Sheets

HYDROGEL CONDOM

FIELD

The disclosure relates generally to prevention of disease and prevention of pregnancy. The disclosure relates specifically to condoms.

BACKGROUND

Condoms have been used for the prevention of disease and pregnancy. A frequent complaint with male condoms is the decreased pleasure. Therefore, individuals can be reluctant to use condoms due to the perceived decrease in sexual pleasure.

Seat belts, smoke alarms, and vaccinations are preventative measures intended to reduce health risks. Yet, their use does not eliminate all risk. Similarly, latex condom use does not provide 100% protection against transmission of STDs but receives frequent complaints about decreased pleasure. Even though several alternative condoms are in the market (e.g. natural membrane (skin) condoms), they do not offer the same level of protection against STDs. A recent report showed the great promise of a graphene condom. A fundamental issue is that graphene is an inorganic material and its efficacy upon direct incorporation into human health applications remains an open question. Overwhelming evidence has already shown the adverse effect of using graphene in human health, specifically on skin. A team of biologists, engineers, and material scientists examined graphene's potential toxicity as it can easily pierce through cell membranes in human lung, skin, and immune cells (Li. et al. 2013, Lanphere et al. 2014, Fusco group). At this stage, the material safety data sheet governing the industrial use of graphene is incomplete. Graphene listed as a potential irritant of skin and eyes, and potentially hazardous to breathe in or ingest. Hence the possibility of direct contact and mechanical action of graphene sheets against soft tissue may be a feature prohibiting its use in condoms. Good electrical and thermal conductivity that make graphene unique may also have unintended consequences and pose major problems in graphene-based condom design. It may ultimately offset the advantage of the large tensile strength available with the use of graphene. The electronic and structural features of inorganic graphene sheets that are attractive for semiconductor and opto-electronic applications may not be directly transferable to condom design and medical applications. In addition, Origomi Company showed a possibility of using silicone for the condom material; again the material itself shows a health concern due to recent evidence of silicone induced toxicity or infection (Ahmed 2013, Stuck et al. 2004, Narini et al. 1995). Silicone has not become popular due to poor surface wettability. In addition, transport of drugs in the silicone can be diffusion limited and the release profiles are complex.

A number of scientists are working on hydrogel based condoms and refining the hydrogel characteristics. The use of hydrogels has become popular due to their viscoelastic characteristics, biocompatibility, amiability of fabrication into specific shapes and their ability to allow transfer of gases and nutrients. It has been proven to be a safe material for skin contact (already in use for eye contact lenses—the most sensitive part in human body), and as such is the safest material for designing a new generation condom. The unique properties of hydrogels such as their stability in aqueous media and softness make them ideal for several biological applications such as tissue engineering, wound healing, controlled drug release, and even contact lenses. Hydrogel systems also have attracted increasing attention as tissue engineering scaffolds and for the sustained release of drugs (Park et al. 2013; Zhang et al. 2005). In particular, the use of hydrogel as scaffolds for tissue engineering is promising because of similarities in physical properties with natural tissues (Kikuchi & Okano 2002, Qui & Park 2001). Unlike latex, they can increase the sensitivity to touch, incorporate lubrication in the system, and be coupled to other components, such as stimulants and anti-viral drugs.

Scientists have investigated a variety of drug delivery systems aimed at better skin permeability of several antioxidants. Successful encapsulation and release of bioactive components such as quercetin and capsaicin (Pool et al., 2013; Park et al., 2013; Cho et al., 2012; Fang et al., 2002). Maximal drug delivery can be acquired using various inexpensive, natural, and non-toxic synthetic biocompatible polymers that exist as a three-dimensional hydropolymer (hydrogels). The unique properties of hydrogels include stability in aqueous media and softness. This is ideal for biological applications such as tissue engineering, wound healing, controlled drug release, and even contact lenses. A hydrogel patch containing capsaicin has been used to treat neck pain (Cho et al., 2012). Facial solid hydrogel masks can deliver Vitamin C and polyphenols to skin.

Several lines of evidence support a role of a naturally available diet or plant extract in sexual enhancement. One of the flavonoid antioxidants, quercetin (also found in rhizomes of a plant used for sexual enhancement in Thailand), is used for enhancing sexual pleasure. In vitro and in vivo studies (Kataria S et al., 2013) demonstrated the ethnopharmacological evidence of *Corchorus depressus* extract (contains quercetin) as a sexual stimulating agent. In addition, quercetin showed vasorelaxing effects on mice, guinea pig as well as human corpus cavernosum (CC) strips (Ertuğ P U et al., 2010; Hnatyszyn O et al., 2004; Jansakul C et al., 2012). A recent paper by Kukongviriyapan et al. showed that quercetin has a vascular protective effect associated with eNOS upregulation. NOS not only initiates erection (facilitates blood flow in penis resulting in smooth muscle relaxation) but also provides sustained maximal erection.

It would be advantageous to have a condom that would enhance sexual pleasure, therefore increasing condom use throughout a population. Increased condom use would serve to prevent disease and prevent pregnancy.

SUMMARY

An embodiment of the disclosure is a condom comprising a hydrogel and an antioxidant. In an embodiment, the ratio of the water/polymer is 86%/14% (w/w). In an embodiment, the antioxidant is quercetin. In an embodiment, the hydrogel comprises cross-linked multi-networks. In an embodiment, the hydrogel comprises sulfated beta-cyclodextrin, polyacrylamide, and alginate. In an embodiment, the hydrogel is comprised of ionic bonds and covalent bonds. In an embodiment, the ionic bonds are 1) sulfated beta cyclodextrin with high negatively charge density and positively charge polyacrylamide and 2) calcium ion and alginate. In an embodiment, the covalent bonds are 1) covalent crosslinks between polyacrylamide chains by N, N-methylenebisacrylamide and 2) amine groups on polyacrylamide chains and carboxyl groups on alginate chains. In an embodiment, the antioxidant is released by stretching of the hydrogel. In an embodiment, the antioxidant is quercetin. In an embodiment, the condom is capable of providing an increase in sexual pleasure when worn over not wearing a condom. In an embodiment, the condom is impenetrable to sperm. In an embodiment, the antioxidant is antiviral.

An embodiment of the disclosure is a method of manufacturing the condom of claim 1 comprising embedding the antioxidant into the hydrogel. In an embodiment, the condom of claim 1 comprising encapsulating the antioxidant into the hydrogel. In an embodiment, the hydrogel comprises sulfated beta-cyclodextrin, polyacrylamide, and alginate. In an embodiment, the hydrogel comprises ionic bonds comprising are 1) sulfated beta cyclodextrin with high negatively charge density and positively charge polyacrylamide and 2) calcium ion and alginate. In an embodiment, the hydrogel comprises covalent bonds comprising 1) covalent crosslinks between polyacrylamide chains by N, N-methylenebisacrylamide and 2) amine groups on polyacrylamide chains and carboxyl groups on alginate chains. In an embodiment, the antioxidant is quercetin. In an embodiment, the condom is capable of providing at least one of the group consisting of antiviral activity, enhanced sexual pleasure, and impermeability to sperm.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

In order that the manner in which the above-recited and other enhancements and objects of the disclosure are obtained, a more particular description of the disclosure briefly described above will be rendered by reference to specific embodiments thereof which are illustrated in the appended drawings. Understanding that these drawings depict only typical embodiments of the disclosure and are therefore not to be considered limiting of its scope, the disclosure will be described with additional specificity and detail through the use of the accompanying drawings in which:

FIG. 7 depicts a graph of tensile stress of hydrogel sheets. Stress-stretch curves of gel film 1 and 2. The mechanical tests of gel were carried out in a tensile machine (Instron, model 3342). Strain=Extension/initial length Extension Gel film 1 was stretched to rupture at extension 100. Gel film 2 was stretched to rupture at extension 93.

FIG. 9 depicts Release of quercetin by stretching gel. A) Schematic of the molecular stretching of the hydrogel. B) The images show the gel was stretched to 220% of its initial length. C) The images show the gel was stretched to 220% of its initial length. The quercetin was released on the gel surface by stretching gel. At different time points, the quercetin sample solution released from gel was picked up by pipet tip for analysis. D) Blue line: the gel film was stretched to 220% of its initial length; red line: no stretch. At different time points, the quercetin sample solution from gel surface was added in DMSO solution, quercetin was detected by UV absorbance peak at 375 nm.

DETAILED DESCRIPTION

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure. In this regard, no attempt is made to show structural details of the disclosure in more detail than is necessary for the fundamental understanding of the disclosure, the description taken with the drawings making apparent to those skilled in the art how the several forms of the disclosure may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary 3$^{rd}$ Edition.

The effectiveness of any biomedical prevention technology relies on both biological efficacy and behavioral adherence. Several novel condom products may ultimately fail if general population does not use the product. Central to this problem may be inadequate awareness and conceptualization of how product properties themselves impact user experience and adherence. The condom industries are intensively focused on the development of new types of attractive condoms. Yet, even if highly efficacious, the public health impact will depend on actual use (i.e., adherence) by at-risk individuals. That is, the ultimate effectiveness of any biomedical prevention technology to reduce HIV incidence or unwanted pregnancy will require both biological efficacy and behavioral adherence.

Focusing on the material of the condom itself is not enough for developing next generation condom. As some of the recent untreatable STDs show a greater threat to mankind than cancer (e.g. HIV), adding an additional safety net (in addition to a condom) for the prevention of STDs is vital. Also, because the condom breakage rate was determined to be as high as 12.9% in some studies (Trussell et al. 1992, Grasso et al. 2016), an antiviral compound, such as a multi-functional antioxidant quercetin, is included within the condom material. Success of several viral entry inhibitors are prohibited by high manufacturing costs and formulation despite their potency and specificity. Therefore, there exists a gap in the HIV prevention pipeline that underscores the need for a mass producible, inexpensive, broad-spectrum, and biocompatible viral inhibitor within the condom material. For this purpose, quercetin shows great potential. Quercetin, recognized for its sexual pleasure enhancing power, is an established antioxidant with anti-viral/anti-microbial/anti-fungal activity. A variety of evidence exists that effective drug delivery can be achieved using various inexpensive, natural, and non-toxic synthetic biocompatible polymers through the use of three-dimensional hydropolymers (hydrogels). A durable, stretchable hydrogel material with an antioxidant with anti-HIV and aphrodisiac properties embedded in it has been created. The user is therefore encouraged to use a safe, reliable condom with antiviral properties.

Various antioxidants are used as stimulants to increase sexual pleasure and intimacy in many countries. The constant search for flavonoid (natural plant based) antioxidants is attractive because they are readily accessible, affordable, and less toxic. If individuals only consume these products orally and do not use a condom (a frequent complaint with male condoms is the decreased pleasure), there can be an unintended pregnancy or transmission of sexual transmitted infections (STIs). The issue is how to deliver the antioxidant to the genital tissue in conjunction with condom.

A goal is to develop a condom which can prevent human immunodeficiency virus (HIV) and others responsible for STIs. The number of HIV-infected people and AIDS patients continues to increase, especially in the developing countries. A variety of flavonoids were evaluated for anti-HIV activity (e.g. block transmission, adsorption, integration, replication etc.). Interestingly, quercetin has been shown to block the infection as well as to inhibit the reproduction of the virus in infected cells. Mahmood et al. showed that quercetin inhibited the HIV-infection by preventing binding of gp120 to CD4 and this irreversible interaction with virus prevents the entry. In addition, quercetin can also inhibit HIV1 entry co-receptor CCR5 in normal PBMC in a dose dependent manner (Nair et al., 1995). Reverse transcriptase of HIV has been demonstrated to be important for the viral replication. This enzyme is necessary for an HIV-infected cell to replicate and reproduce more infected cells. Several studies demonstrated quercetin as one of the most potent (higher EC50) flavonoid for inhibiting HIV replication (Ono et al., 1990; Lo et al., 2003; Kashiwada et al., 2005). It also acts as a potent integrase and protease inhibitor (high EC50) (Fesen et al., 1993; Kim et al., 1998; Xu et al., 2000). Additionally, quercetin promotes the expression of anti-inflammatory cytokines that inhibit viral production and the ability of offspring viruses to infect other cells. It has been shown to inhibit the production of pro-inflammatory cytokines such as tumor necrosis factor alpha (TNF-α) that promote HIV activity, while elevating an anti-inflammatory levels (IL13) that inhibits infection (Nair et al., 2009). Quercetin is in a Phase 1 trial for another STI (HCV). Blocking the transmission of virus is a focus. Hydrogels with varying concentrations of different kinds of monomer units in conjunction with pore size control can be synthesized for the hydrogel condom. The small pore size of our hydrogel will block the HIV or other viruses and sperm entry. However, it is an advantage if quercetin blocks the replication of the virus in case of an accidental infection.

Mechanical properties of hydrogels can include minimal elasticity and brittleness. A highly elastic hydrogel is possible that can withstand high shear stresses and can stretch to over 20 times its length at low thickness (Sun et al., 2012). A hydrogel has been developed which can be stretched up to 30 times its length at low thickness. The hydrated and soft nature of these hydrogels ensures that a condom of this material would be naturally well lubricated. This would also simulate the vaginal environment in a superior manner as compared to latex condoms that cause a reduction of tactile sensation and attenuate heat transduction (Randolph et al., 2007).

A polymer hydrogel with extraordinary mechanical properties was synthesized by ionically and covalently cross-linked networks. The polymer hydrogels show highly stretchable and tough properties. Furthermore, the network of covalent crosslinks preserves the memory of the initial state, so that much of the large deformation is removed on unloading. In addition, the embedded cyclodextrin can use to encapsulate small molecules antioxidants by host-guest chemistry. In addition, a successful encapsulation of quercetin was carried out using a host-guest chemistry.

Figure 1:
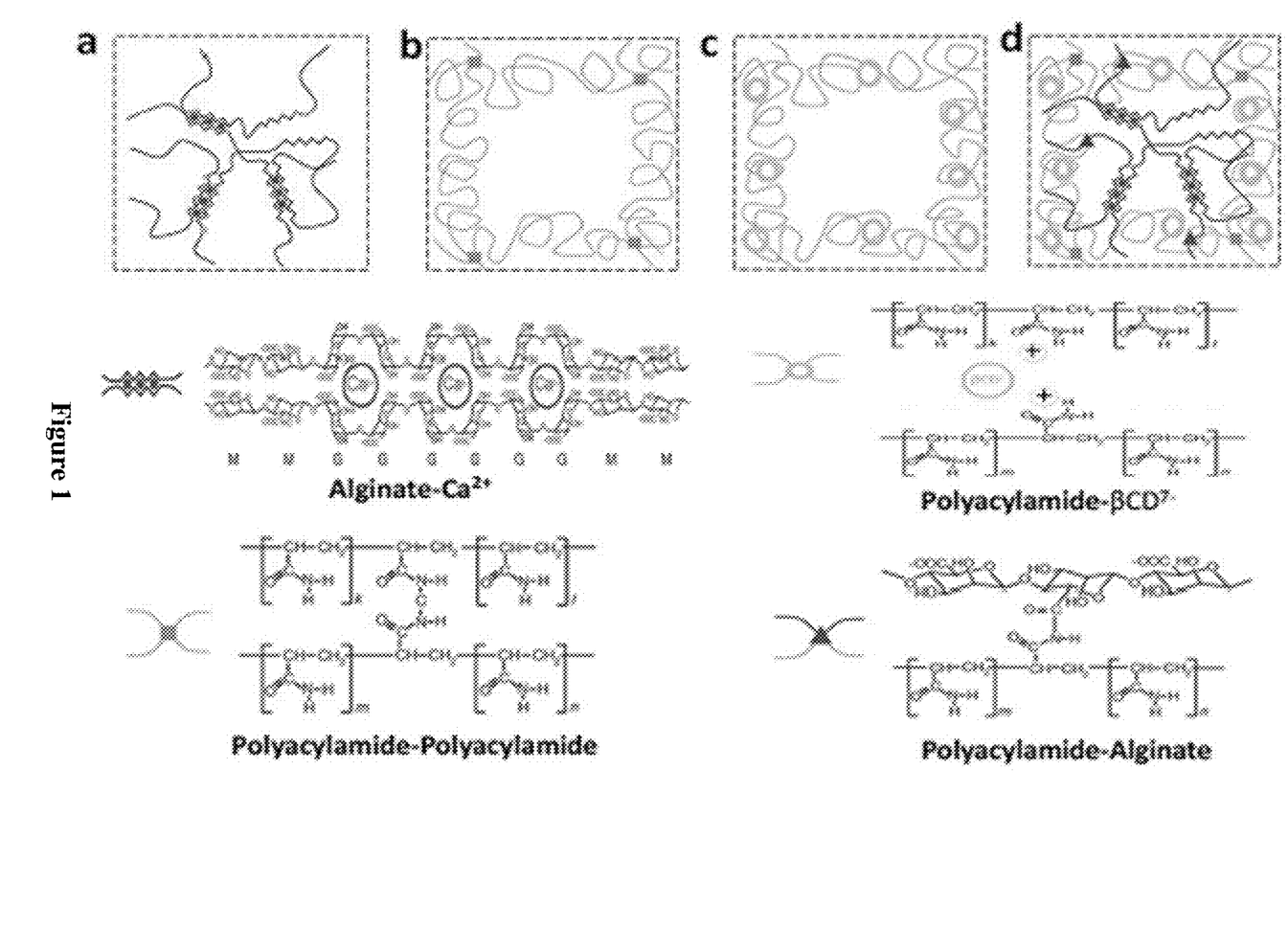
FIG. 1A-1D depict schematics design of multi-network polymer hydrogel: A) G blocks of alginate gel on different polymer chains form ionic crosslinks through $Ca^{2+}$ (red circles). B) In a polyacrylamide gel, polymer chains form covalent crosslinks through N, N-methylenebisacrylamide (MBAA, green squares). C) In a polyacrylamide hybrid gel, polymer chains form ionic crosslinks through sulfated beta-cyclodextrin anion and polyacrylamide cation (yellow circles). D) In an alginate-polyacrylamide hybrid gel, two types of polymer network are intertwined, and joined by covalent crosslinks (blue triangles) between amine groups on polyacrylamide chains and carboxyl groups on alginate chains.
Figure 2:
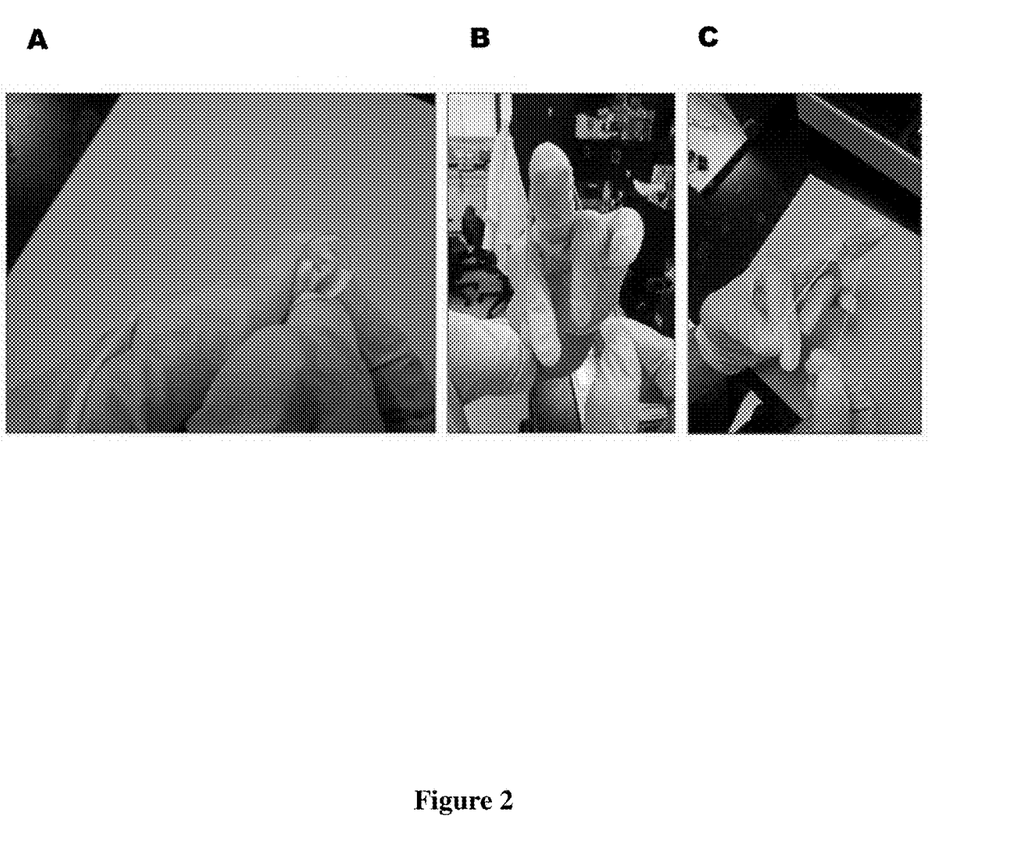
FIG. 2A-2C depict gels with water/polymer 86%/14% (w/w) ratio very tough. The gel is able to withstand a high level of torsion deformation and has high elasticity. The multi-network hybrid hydrogel is highly stretchable, elastic and bendable. The gel in photographs is rod shaped with 4 mm in diameter. A. bending of the gel at a bending angle 180°; B. and C. stretching and bending and torsion deformation (20 times initial length and 180° bending angle).
Figure 3:
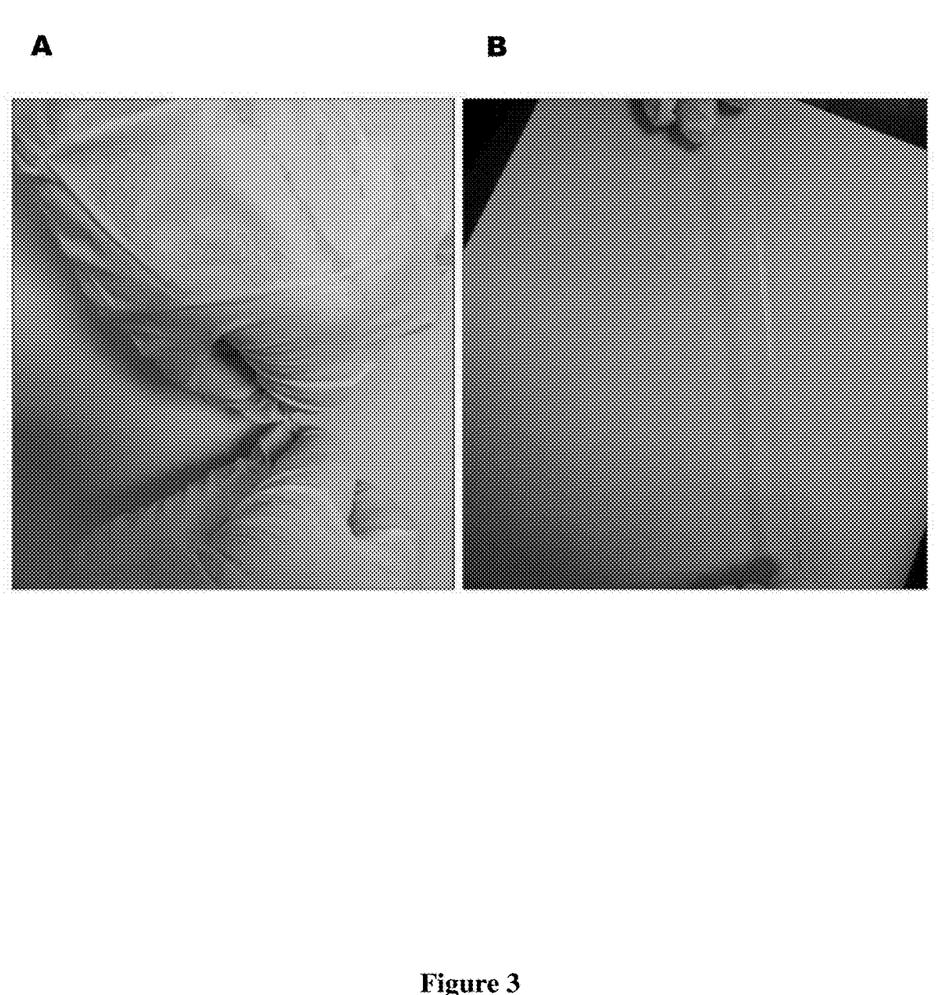
FIG. 3A-3B depict the transparency and high elasticity of the gel (water/polymer 86%/14%). The hydrogel withstands extreme stretching (from A) to B)). It can be stretched to 30 times of its initial length.
Figure 4:
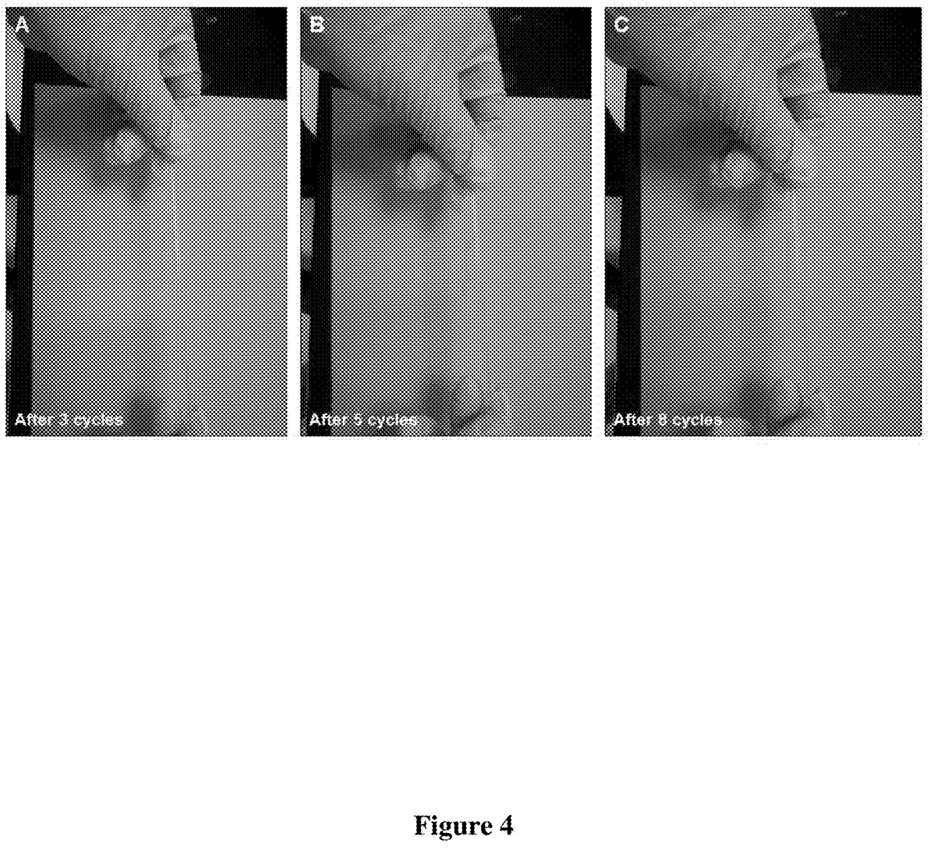
FIG. 4A-4C depict a multi cycle stretch test (30 times its initial length). A) Length of hydrogel after 3 cycles of stretching. B) Hydrogel length after 5 cycles of stretching. C) Length of hydrogel after 8 stretch cycles.

Design of the multi-network polymer hydrogel: A novel polymer hydrogel was created with significant mechanical properties. The extremely stretchable and tough hydrogel was synthesized by ionic and covalent cross-linked multi-networks (FIG. 1). The polymer gels consist of sulfated beta-cyclodextrin, polyacrylamide, and alginate. The sulfated beta-cyclodextrin is well known as a host molecule that can form a 1:1 inclusion complex with small antioxidant guest molecule quercetin. This is supported by molecular modeling. In an embodiment, one or more different antioxidants can be used. The 3D multi-network structure was formed through two types of ionic bonds (sulfated beta-cyclodextrin with high negatively charge density and positively charged polyacrylamide, as well as calcium ion and alginate) and two types of covalent bonds (covalent cross-links between polyacrylamide chains by N, N-methylenebisacrylamide (MBAA), as well as covalent crosslinks between the amine groups on polyacrylamide chains and carboxyl groups on alginate chains). The multi-network design will benefit those including stretchability, toughness, and recovery after gel stretching. Preparation of the hydrogel: The hydrogel was then prepared using the above described multi-network schematic. The hydrogel displayed superb flexibility (FIG. 2), which can bend freely in a wide 0-180° range of bending angle and also is repeatable and reversible in forward (bending) and reverse (bending back) directions. After the forward and reverse bending over 200 cycles, the gel retained its outstanding property without cracking and wrinkling. Surprisingly, after stretching, the tough gel can also bend and twist at any direction (FIG. 2). FIG. 3 illustrates the 4 mm in diameter rod-shape gel being readily stretched to 30 times its initial length, and after relaxation, quickly restored to the original length and size (FIG. 3). Furthermore, the hydrogel can withstand repeated stretch cycles and maintain its form (FIG. 4). The elasticity and stretchability of the hydrogel are similar to the properties of rubber.

Figure 5:
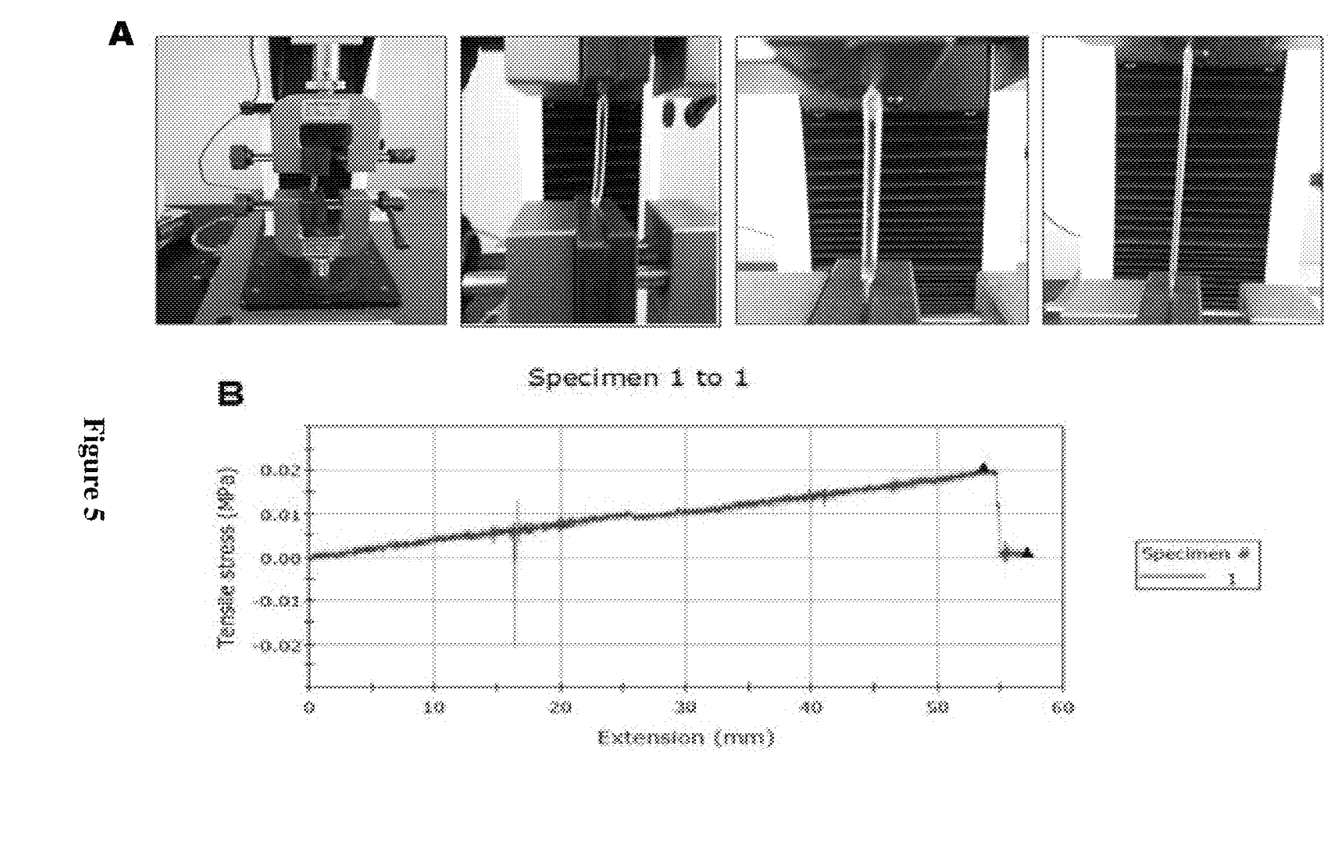
FIG. 5A-5B depict a gel rod in tensile machine (stretched to 26 times of its initial length). The multi-network polymer hydrogel rod with diameter 0.5 cm was prepared. The two ends of the gel rod were clamped in a tensile strength machine (Instron model 3342) and its mechanical properties tested. A) Hydrogel being stressed on tensile machine. B) Quantification of hydrogel tensile stress during testing on tensile machine. Stress-stretch curve showed that the multi-network polymer hydrogel rod (initial diameter 0.5 cm) was stretched to 26 times its initial length.
Figure 6:
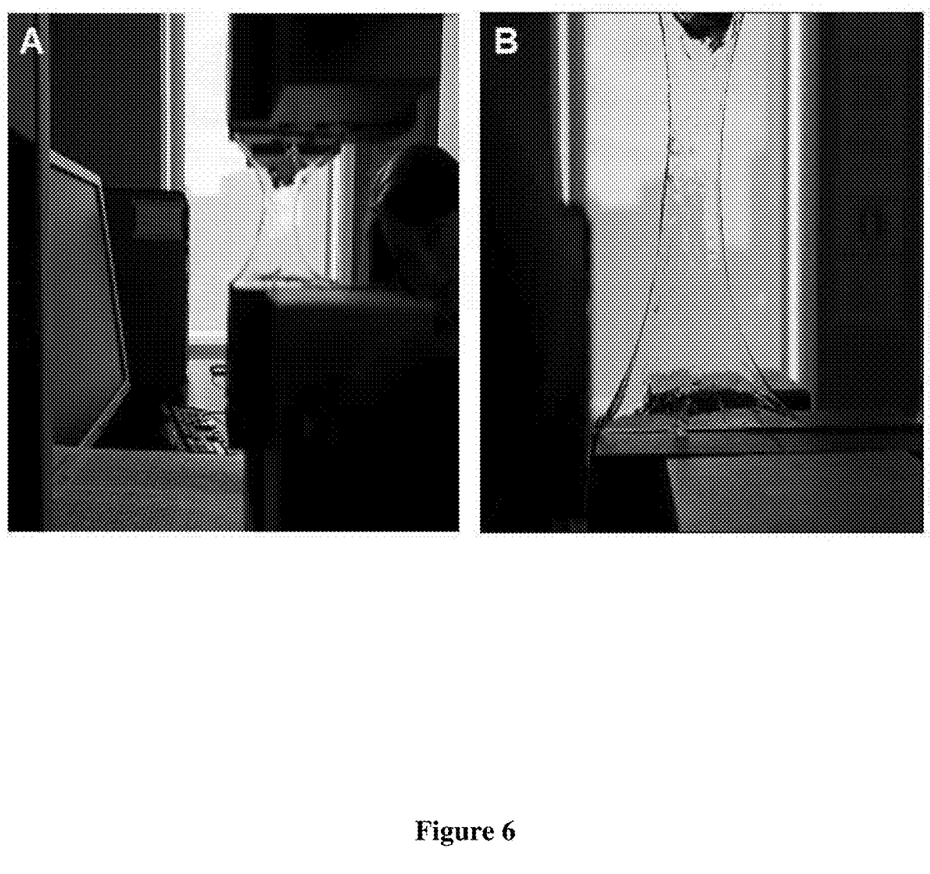
FIG. 6 depicts a hybrid gel film subjected to tensile stress (stretched to 30 times of its initial length). The multi-network polymer hydrogel film was fixed with two rigid clamps in the Instron, model 3342.

Measurement of tensile stress: The tensile strain tests were further performed in air using a tensile machine with a 500-N load cell. In the process, the stretch rate was kept constant at 2.0 min$^{-1}$. In FIGS. 5 and 6, the gel rod and the gel film could be stretched to 26 times and 30 times their initial length. The extreme stretching ability and toughening of this hybrid hydrogel should be ascribed to the multi-networks formed by both the ionic cross-linking and the covalent cross-linking, in which two types of reversible ionic crosslinking with differential bond energy, sulfated β-cyclodextrin/polyacrylamide and $Ca^{2+}$/alginate, dissipates mechanical energy, while two types of covalent cross-linkings of polyacrylamide/polyacrylamide and polyacrylamide/alginate maintain elasticity.

Figure 7:
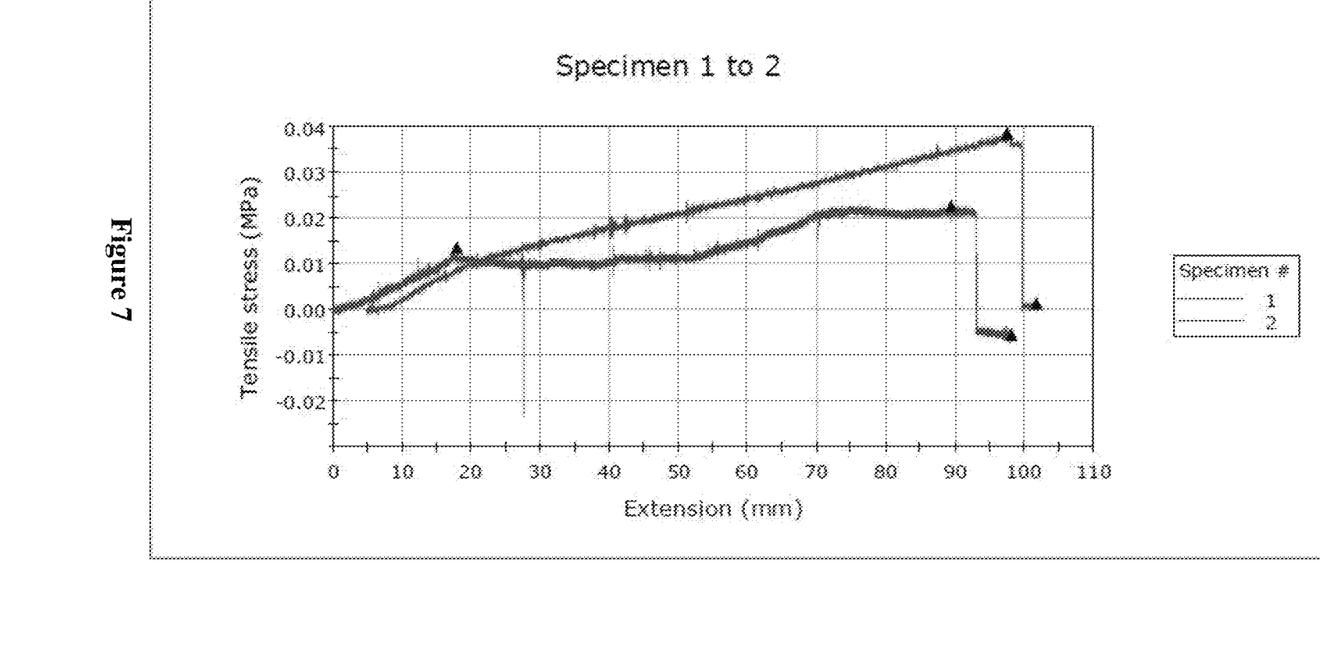

Hydrogel sheets can be generated and withstand extreme tension stress: The mechanism is supported by the result of FIG. 6. After the first loading and unloading, the multi-network hydrogel film was stretched to 27.9 times its initial length when the second loading was applied immediately, indicating a fast and good recovery. Although the second immediate loading gel dissipated energy ineffectively (FIG. 7, Specimen #1 strain curve), the gel film had no fracture or wrinkling during stretching.

Figure 8:
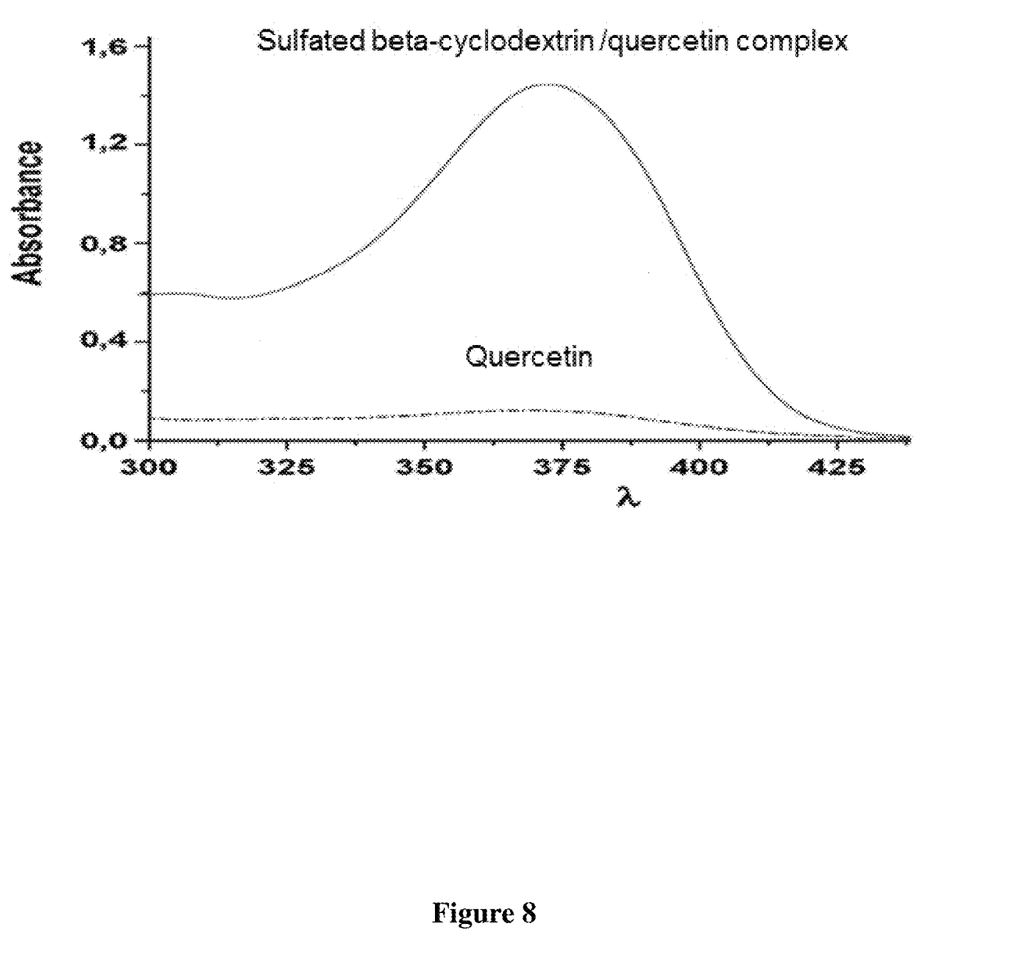
FIG. 8 depicts a graph of sulfated beta-cyclodextrin formed 1:1 complex with antioxidant quercetin, showing quercetin can be encapsulated in the gel. Antioxidant quercetin had a UV absorbance peak at 375 nm (dashed line). In the presence of sulfated beta-cyclodextrin, the absorbance increased. The sulfated beta-cyclodextrin can form 1:1 complex with quercetin through host-guest chemistry. The results showed quercetin can be encapsulated in the gel.
Figure 9:
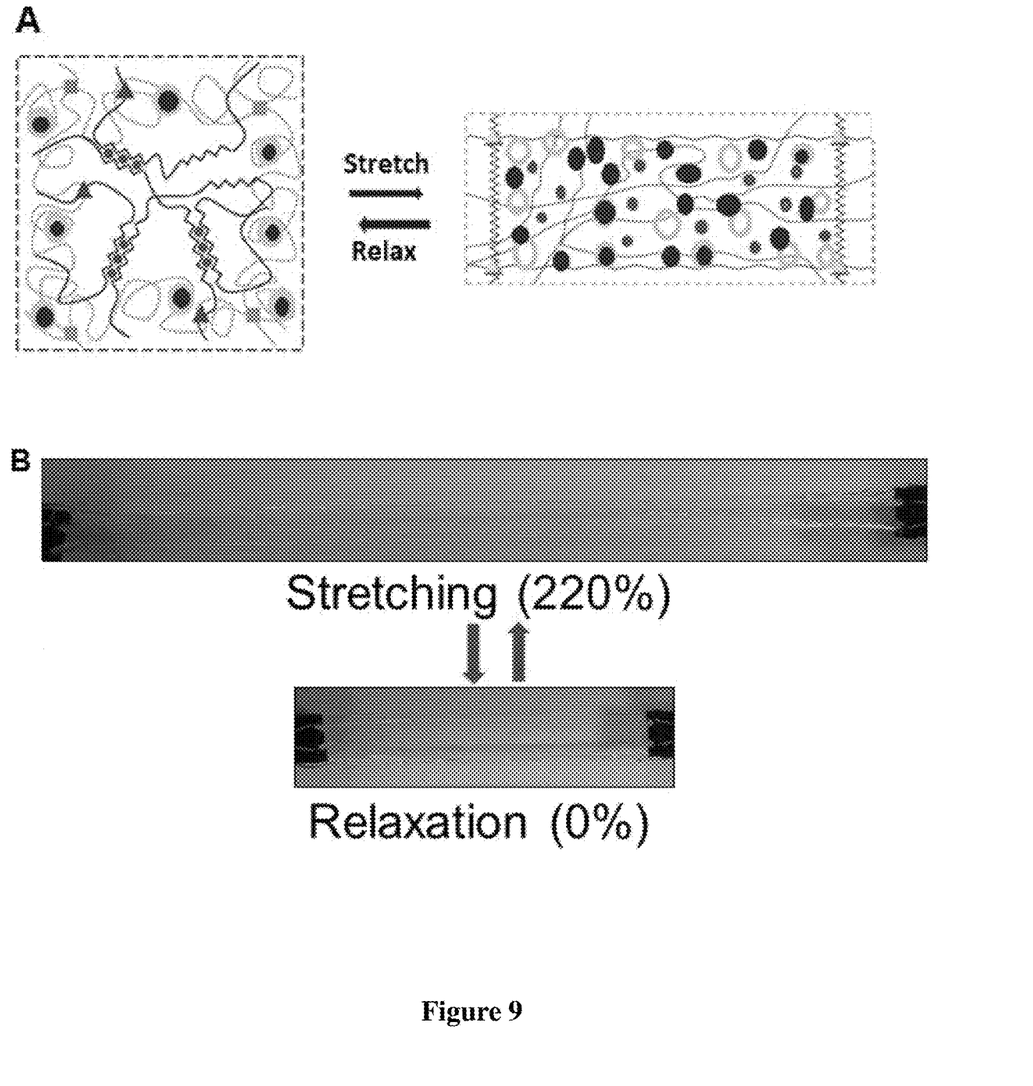
Figure 10:
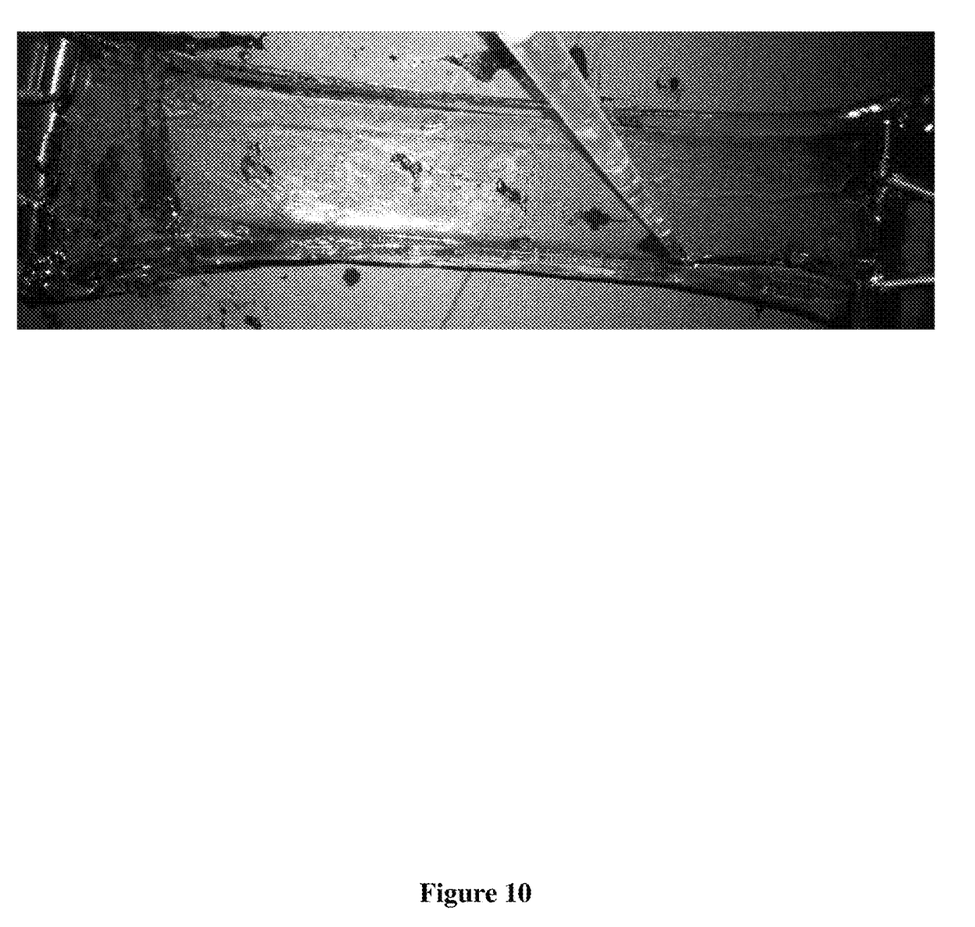
FIG. 10 depicts the hydrogel stretched 400% of its initial length. The image shows the gel was stretched to 400% of its initial length. Doxorubicin was released on the gel surface by stretching gel. At different time points, the quercetin sample solution released from gel was picked up by pipet tip for analysis.

Embedment of quercetin in hydrogel and its release: The sulfated beta-cyclodextrin in the crosslinked polymer hydrogel allows drug molecules, even hydrophobic compounds, to incorporate into it through host-guest interaction. An encapsulated-quercetin hydrogel film was prepared (FIG. 8). As known, quercetin is sparingly soluble in water (~1.3 µM), sulfated beta-cyclodextrin with high inclusion ability can significantly enhance its solubility (42 µM in 1 mM sulfated beta-cyclodextrin, 73 µM in 2 mM sulfated beta-cyclodextrin) as shown in FIG. 8. The high equilibrium binding constant of the sulfated β-cyclodextrin/quercetin complex ($K_f$=2.53×10$^4$ M$^{-1}$ at 25° C.) permits encapsulation of high concentration of quercetin in gel. The fabrication of the quercetin hydrogel is similar to that mentioned above, except for alternative sulfated beta-cyclodextrin with 1:1 sulfated beta-cyclodextrin/quercetin complex. The resultant hydrogel attained similar high fracture toughness and stretching ability in the presence of quercetin (FIG. 9). Quercetin is released from the hydrogel by stretching 220% (FIGS. 9C & 9D) and 400% of its initial length (FIG. 10).

In an embodiment, an antioxidant embedded hydropolymer has been created for use in a condom. The present disclosure details incorporation of a flavonoid antioxidant into solid hydropolymer condom to enhance sexual pleasure and regular usage. In an embodiment, the flavonoid is quercetin. In an embodiment, a different antioxidant can be used. In an embodiment, the antioxidant is selected from *panax ginseng* or *satureja khuzestanica*. In an embodiment, any aphrodisiac can be used. Pharmacological evaluations of these components have shown their ability to activate neurotransmitter(s) resulting in smooth muscle relaxation and increase arterial flow as well as energize nerve endings. Antioxidants preserve the nitric oxide needed to dilate blood vessels in genital tissues leading to sexual arousal. Transdermal delivery of these components can be considered as an alternative to the oral route in order to avoid any adverse side effects, to shorten onset time, and to sustain the effect for longer periods. Evidence demonstrates the anti-HIV properties of flavonoid antioxidants.

In an embodiment, components other than quercetin and capsaicin can be used in the hydrogel condom. In an embodiment, more than one component can be present in the hydrogel condom at one time. In an embodiment, mechanisms other than encapsulation can be used to include the component in the hydrogel condom. In an embodiment, the component is embedded in the hydrogel condom. In an embodiment, the hydrogels have a different ratio of water/polymer than 86%/14% (w/w). In an embodiment, the ratio is 50%/50%. In an embodiment, the ratio is 75%/25%. In an embodiment, the polymer comprises polyacrylamide and alginate. In an embodiment, the polymer comprises β-cyclodextrin. In an embodiment, the antioxidant embedded hydrogel can be used for other than a male condom. In an embodiment, antioxidant embedded hydrogel can be used for a female condom. In an embodiment, the composition of matter can be used as an anti-HIV condom. In an embodiment, the composition of matter can provide protection from HIV, increase sexual pleasure, and stop unwanted pregnancy. In an embodiment, the hydrogel will be prepared as a condom. In an embodiment, the condom will be tested for any side effects and anti-HIV effect.

This innovative condom will be effective to increase smooth muscle relaxation, stimulate nerve endings as well as maintain erection leading to ultimate sexual pleasure during intercourse while preventing STIs and unwanted pregnancy. Current market trends show that a wide variety of male condoms, lubricants, and supplements are already in place, but the hydrogel condom with an antioxidant allows users to purchase only one product to enhance sexual pleasure though vascular simulation properties of antioxidants, while maintaining the protective properties of the male condom. The roles of quercetin with respect to endothelial physiology and HIV protection along with stretchable nano-pored hydrogels are ideal for production of a hydropolymer-based male condom implanted with a natural flavonoid antioxidant, quercetin.

EXAMPLES

Example 1

The quercetin nanoencapsulation system for enhanced aqueous phase solubility will be prepared. This involves preparation of a 500 µM quercetin solution into liposomes by thin-film hydration method (Muramatsu et al., 1994; Park et al. 2013). Stability and efficiency of encapsulation of this method has been optimized. Depending on the need of quercetin release from the hydrogel to stimulate the nerve/NOS production/transdermal permeability, adjustments can be made in Example 3.

Example 2

The hydrogel is prepared by a combination of methods. Sun et al., 2013 (using ionic alginate and covalent polyacrylamide crosslinks to make a highly elastic and fracture-resistant hydrogel) and Izawa et al., 2013 (using β-cyclodextrin derived crosslinks to create a hydrogel that should release loaded quercetin in response to a minimal pressure—simply by skin contact pressure or rubbing) showed two unique hydrogels. Addition of β-cyclodextrin will enhance the fast release of quercetin (target less than 10 sec) in conjunction with normal diffusion mediated antioxidant delivery. The design will be optimized to make the pore size as low as possible (target≤30 nm; Varghese et al. made 5-20 nm pore sized hydrogel) to block any viral entry. The quercetin loaded liposomes in hydrogel will be prepared. The incorporation efficiency of liposomes into hydrogel will be assessed. In another embodiment, the quercetin loaded hydrogel will be prepared and the incorporation efficiency of quercetin will be assessed.

Example 3

Stability test for released quercetin from hydrogel will be performed and release time optimized (target should be in seconds). The release of quercetin from hydrogel in a phosphate buffer solution will be determined and its bio-accessibility assessed. Viral leakage tests will be conducted to confirm protection against viral entry. In vivo experiments will be performed. The relaxation effect and signaling pathways in rat CC will be evaluated. Topical application of the hydrogel will then be carried out in shaved mice and any visible skin changes observed. The transdermal permeation of quercetin will be determined using reversed phase high performance liquid chromatography.

Example 4

Optimization of Quercetin Encapsulation in the Hydrogel and Refinement of the Quercetin—Embedded Hydrogel A 1:1 inclusion complex between sulfated β-cyclodextrin (β-CD) and quercetin was used. To further probe the mode of interaction between quercetin and β-CD, a computer aided molecular modeling study will be conducted both in vacuo and in water. Zheng et al. (2005) demonstrated that the aqueous solubility and chemical stability of quercetin can be substantially augmented via complexation with β-CDs, particularly with sulfobutyl ether β-cyclodextrin. The equilibrium binding constants and thermodynamic parameters determined by phase solubility study as well as the significant chemical shift changes of quercetin observed with the various β-CDs in 1H-NMR analyses are consistent with the formation of inclusion complexes. The hydrogel embedded quercetin encapsulation will be optimized with molecular modeling simulations followed by 1H-NMR spectroscopic analysis and chemical stability assays. The idea is to create a hydrogel that should release loaded quercetin in response to a minimal pressure-such as by skin contact pressure or rubbing. Addition of β-CD did enhance the fast release of quercetin (the target is less than 10 secs) in conjunction with normal diffusion mediated antioxidant delivery. To examine the feasibility in achieving a fast quercetin delivery from the hydrogels, kinetics of quercetin will be tested with different concentrations. In vitro release tests will be performed. An optimized condom material that combines the robust mechanical strength of the hydrogel with the rapid release of quercetin will be prepared. The design will be optimized and the hydrogel pore size adjusted such that STDs and sperm will not penetrate. In addition, it will be validated that the hydrogel will be able to encapsulate or entrap quercetin without altering the condom's functional activity. Adverse effects on skin and induction of transdermal permeability will also be addressed if necessary.

Example 5

Dermal Application of Quercetin Embedded Hydrogel, Side Effects, and Biological Response Several groups have investigated nanoparticles as a topical delivery system for quercetin and showed a higher permeation ability, significantly increased accumulation of quercetin in the skin, and maintenance of its functional activity. Hydrogels are employed as modern vehicles in topical application and often provide a fast release of the drug. The optimized formulation of the quercetin embedded by the hydrogel is expected to be compatible with most living tissues. The pharmacodynamic determination will be carried out using bioengineering methods (e.g. transepidermal water loss (TEWL), colorimetry) in a murine model (Fang et al. 2002). TEWL refers to the rate at which quercetin migrates from the viable dermal tissues to the external environment. Since the value of quercetin TEWL increases logarithmically with skin surface temperature, TEWL will be useful for evaluating the degree of irritation caused by quercetin (Fang et al. 1996, 2002)). Surface color can be quantified through colorimetry using the Commission Internationale de I'Eclairage system. Both local burning sensation and skin irritation will be monitored. As shown in earlier studies, hydrogels show a low Primary Irritation Index. The advantage of this system is that it is adapted to the nonlinear color perception of the human eye. This technique will be useful in determining skin erythematous responses or any visible skin changes caused by quercetin or hydrogel. Either of these are again unlikely as both are non-toxic and non-allergic components. The transdermal permeation of quercetin will be determined using reversed phase high performance liquid chromatography. The relaxation effect, erection function, histological, and immunohistochemical analyses in rat corpus cavernosum will be evaluated. Topical delivery of drugs has resulted in unanticipated toxicities, which have been linked to an increased risk of HIV acquisition in large clinical trials. For example, nonoxynol-9, which has been safely used for decades as a contraceptive, was found to increase the risk of HIV, possibly through disruption of the epithelial barrier and induction of an inflammatory response. Similarly, 6% cellulose sulfate gel was also associated with a trend toward increased HIV risk, which resulted in early termination of the clinical trial. However, this is unlikely here as an antioxidant is being used as a drug. The activation of signaling pathways including nitric oxide synthase expression and inflammatory cytokine or chemokine genes (IFN-γ, IL-1β, IL-6, MCP-1, MIP-1α, RANTES, CXCL-1, MIP-2, TNFα) will be investigated at several short and long term time points. All the experiments will be assessed with the hydrogel itself (without quercetin) and the adjacent untreated skin area. In addition, activity of quercetin embedded hydrogel will be investigated in Example 6.

A stability test for released quercetin from hydrogel can be performed and release time (target should be in seconds) can be optimized. The release of quercetin from hydrogel in a phosphate buffer solution and assess its bio-accessibility can be determined. Viral leakage tests will be conducted to confirm protection against viral entry. In vivo experiments will be performed. The relaxation effect and signaling pathways in rat corpora cavernosa (CC) will be evaluated. Topical application of the hydrogel will be carried out in shaved mice and any visible skin changes observed. In addition, the transdermal permeation of quercetin will be determined using reversed phase high performance liquid chromatography.

Example 6

Analysis of the Quercetin Embedded Hydrogel from a Preventive Aspect

Quercetin represents an interesting class of antiretroviral agents that potentially can inactivate HIV in the vaginal/penile lumen even before HIV reaches susceptible CD4+ cells, preventing heterosexual HIV transmission. There are a limited number of clinical candidates that target HIV entry in comparison to agents that target the enzymatic machinery involved in the viral replication. Interestingly, quercetin not only inhibits HIV-infection by preventing binding of gp120 to CD4 (irreversible interaction with virus prevents entry), it can also inhibit HIV1 entry co-receptor CCR5 (Nair et al 1995). In addition, quercetin was also demonstrated as one of the most potent (higher EC50) flavonoids for inhibiting HIV replication (Ono et al., 1990; Lo et al., 2003; Kashiwada et al., 2005). Additionally, quercetin promotes the expression of anti-inflammatory cytokines that inhibit viral production and the ability of progeny viruses to infect additional cells. It will be investigated whether quercetin released from the hydrogel retains antiviral activity or cytotoxicity through several in-vitro safety and anti-viral activity assays. As the condom will be in contact with the vagina, the anti-viral activity in ectocervical explants exposed to HIV and biocompatibility in human vaginal tissue (commercially available) will be evaluated. To adjust the amount of quercetin, broad-spectrum antiviral assays and activity against laboratory virus strains will be run. Viral leakage tests will be conducted to confirm protection against viral entry. In addition, the effect of seminal fluid on the anti-viral activity of quercetin will be tested.

Example 7

Refinement of Quercetin Embedded Hydrogel

The condom material will be refined (as needed) to optimize the ultimate condition (e.g. porosity for prevention, heat transducing check to increase sensitivity, amount of quercetin, and strength). A comprehensive strength assessment and characterization will be carried out.

Example 8

A Prototype with Mold Dipping Method and Quality Control Check and Refinement of the Product A prototype for this "super condom" can be created using the industrial standard dipping process. Several steps including stretch resistance, pin hole test, volume, and coating will be performed (thickness target is 0.02 mm). Permeability tests will be performed for viral leakage with a method using virus suspension (Kettering 1993). To evaluate the effectiveness of the condom as a barrier to small particles (viral and non-viral) under physiologic conditions more closely resembling actual coitus, a laboratory test system will be used in addition to industrial leakage test. The mechanical properties of the hydrogel will be simultaneously monitored to maintain the strong hydrogel.

Example 9

Development of New Packaging System

One problem with condoms is putting them on incorrectly. Therefore, it is necessary to design an easy-on condom package. The condom could be packaged in an unconventional fashion compared to currently available condoms. It should be in a sealed hydrated wrapper without rolling on the base ring so that the condom can be applied in both directions. Since the improved condom is a homogenous polymer and neither side is lubricated more than other, rolling will not be necessary. Therefore, this well-hydrated and lubricated design ensures an easy and quick application process. In an embodiment, the condom is an inexpensive hydrogel condom with the flavonoid antioxidant quercetin. This condom is reliable, durable, non-toxic, prevents STDs and pregnancy, inexpensive, a sexual enhancer, for all-purpose sexual encounters, and has user-friendly packaging.

Example 10

A number of parameters will be blind tested with users in order to refine products that best meet user needs and demands. This unique condom can be prototyped and tested quickly. In an embodiment, the condom can be packaged in a sealed hydrated wrapper without rolling on the base ring so that the condom can be applied in both directions as it is a homogenous polymer and neither side is lubricated more than other. Therefore, this well-hydrated and lubricated design ensures an easy and quick application process.

The novel condom will encourage regular use by increasing sexual pleasure (sensation and erection molecular mechanism, through a water based non-allergic material) and prevent STDs (by activating anti-viral/anti-bacterial/anti-fungal activity, decreasing the pore size). The condom can be used to prevent STDs or unwanted pregnancy while also increasing regular usage. In an embodiment, this inexpensive condom can be produced at large scale economically, using inexpensive and highly available materials. Female condoms will also be manufactured.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain agents which are both chemically related may be substituted for the agents described herein while the same or similar results would be achieved. All such similar substitutes and modifications apparent to those skilled in the art are deemed to be within the spirit, scope and concept of the disclosure as defined by the appended claims.

What is claimed is:

1. A condom consisting of a hydrogel and an antioxidant, wherein the hydrogel comprises sulfated beta-cyclodextrin, polyacrylamide, and alginate and further comprises ionic bonds, covalent bonds, and cross-linked multi-networks.

2. The condom of claim 1, wherein the hydrogel has a water/polymer ratio of 86%/14% (w/w).

3. The condom of claim 1 wherein the antioxidant is quercetin.

4. The condom of claim 1, wherein the ionic bonds are 1) sulfated beta cyclodextrin with high negative charge density and positively charged polyacrylamide and 2) calcium ion and alginate.

5. The condom of claim 1, wherein the covalent bonds are 1) covalent crosslinks between polyacrylamide chains by N, N-methylenebisacrylamide and 2) amine groups on polyacrylamide chains and carboxyl groups on alginate chains.

6. The condom of claim 1, wherein the antioxidant is released by stretching of the hydrogel.

7. The condom of claim 6, wherein the antioxidant is quercetin.

8. The condom of claim 1, wherein when worn the condom is capable of providing an increase in sexual pleasure as compared to when not wearing a condom.

9. The condom of claim 1, wherein the condom is impenetrable to sperm.

10. The condom of claim 1, wherein the antioxidant is antiviral.

11. The condom of claim 1, wherein the ionic bonds are 1) sulfated beta cyclodextrin with high negative charge density and positively charged polyacrylamide and 2) calcium ion and alginate, and wherein the covalent bonds are 1) covalent crosslinks between polyacrylamide chains by N,N-methylenebisacrylamide and 2) amine groups on polyacrylamide chains and carboxyl groups on alginate chains.

\* \* \* \* \*